United States Patent
Zhao et al.

(10) Patent No.: US 10,787,411 B2
(45) Date of Patent: Sep. 29, 2020

(54) METHOD OF RECYCLING MOTHER LIQUID OF PURE TEREPHTHALIC ACID (PTA) REFINING UNIT

(71) Applicant: TIANHUA INSTITUTE OF CHEMICAL MACHINERY AND AUTOMATION CO., LTD, Gansu (CN)

(72) Inventors: Xu Zhao, Gansu (CN); Tao Shen, Gansu (CN); Tianbao Wang, Gansu (CN); Wanyao Zhang, Gansu (CN); Yuanrui Lu, Gansu (CN); Lilong Xu, Gansu (CN); Min Jia, Gansu (CN); Dongzhao Han, Gansu (CN); Xiaoling Xie, Gansu (CN); Yongning Qiu, Gansu (CN)

(73) Assignee: TIANHUA INSTITUTE OF CHEMICAL MACHINERY AND AUTOMATION CO., LTD, Lanzhou, Gansu (CN)

( * ) Notice: Subject to any disclaimer, the term of this patent is extended or adjusted under 35 U.S.C. 154(b) by 0 days.

(21) Appl. No.: 16/330,230

(22) PCT Filed: May 15, 2017

(86) PCT No.: PCT/CN2017/084350
§ 371 (c)(1),
(2) Date: Mar. 4, 2019

(87) PCT Pub. No.: WO2018/171028
PCT Pub. Date: Sep. 27, 2018

(65) Prior Publication Data
US 2019/0225569 A1 Jul. 25, 2019

(30) Foreign Application Priority Data

Mar. 22, 2017 (CN) .......................... 2017 1 0173237

(51) Int. Cl.
| | |
|---|---|
| *C07C 51/44* | (2006.01) |
| *B01D 3/06* | (2006.01) |
| *B01D 9/00* | (2006.01) |
| *B01D 3/08* | (2006.01) |
| *B01D 3/00* | (2006.01) |
| *C07C 63/26* | (2006.01) |

(52) U.S. Cl.
CPC .............. *C07C 51/44* (2013.01); *B01D 3/007* (2013.01); *B01D 3/065* (2013.01); *B01D 3/08* (2013.01); *B01D 9/0059* (2013.01); *C07C 63/26* (2013.01); *Y02P 20/51* (2015.11)

(58) Field of Classification Search
CPC ......... C07C 63/26; C07C 51/42; C07C 51/43; C07C 51/44; B01D 3/007; B01D 3/065; B01D 3/08; B01D 9/0059; Y02P 20/51; C02F 1/06; C02F 2001/5218; C02F 2101/34; C02F 2103/36; C02F 2301/08; C02F 9/00
See application file for complete search history.

(56) References Cited

U.S. PATENT DOCUMENTS

2002/0183546 A1    12/2002   Sheppard et al.

FOREIGN PATENT DOCUMENTS

| CN | 1278239 A | | 12/2000 |
|---|---|---|---|
| CN | 101139277 | * | 3/2008 |
| CN | 101139277 A | | 3/2008 |
| CN | 101139277 A | | 3/2008 |
| CN | 103670791 A | | 3/2014 |
| CN | 103806964 A | | 5/2014 |
| JP | 2000304375 A | | 11/2000 |
| WO | WO-2009/141968 A1 | | 11/2009 |
| WO | WO-2010/122304 A1 | | 10/2010 |

OTHER PUBLICATIONS

CN101139277 translated (Year: 2008).*

* cited by examiner

*Primary Examiner* — Yevgeny Valenrod
*Assistant Examiner* — Blaine G Doletski
(74) *Attorney, Agent, or Firm* — Muncy, Geissler, Olds & Lowe, P.C.

(57) ABSTRACT

The present invention relates to a method of recycling mother liquid of a PTA refining unit. The present invention recycles waste heat and PT acids of a PTA mother liquid to effectively utilize heat in the PTA mother liquid, solves influence of crystallization of the PT acids on subsequent system, reduces pollution to the environment, and can produce huge economic benefits by using high efficient multistage flash distillation technology, low temperature cogeneration technology, heat pump heating and cooling technology, and low temperature crystallization technology.

12 Claims, 2 Drawing Sheets

METHOD OF RECYCLING MOTHER LIQUID OF PURE TEREPHTHALIC ACID (PTA) REFINING UNIT

TECHNICAL FIELD

The present invention relates to a method of recycling mother liquid of a PTA refining unit, and more particularly, relates to a method of recycling mother liquid waste heat and PT acids of a PTA refining unit in a PTA industrial apparatus. The method is also adapted to recycling of low temperature waste heat of waste water in other industries.

BACKGROUND

In the PTA (Pure Terephthalic Acid) production apparatus, a large amount of waste water containing PT (P-methylbenzoic acid) acids, TA (Terephthalic Acid) solids, and non-condensable gases such as, $H_2$, $N_2$ and the like is often produced in the PTA refining process, and a temperature of the waste water may be as high as 140° C. to 150° C. Currently, the industry mainly processes using a refining tail gas cleaning system. Firstly, high temperature PTA mother liquid from the apparatus enters into an atmospheric flash tower, where flash distillation occurs, steam produced by flash distillation is discharged from a tower top of the atmospheric flash tower to the environment together with the non-condensable gases such as, $H_2$, $N_2$ and the like, then the mother liquid produced by flash distillation is cooled down by the way of air cooling, and the cooled PTA mother liquid enters into subsequent film processing system for use.

The above processing method of PTA mother liquid in the existing industrial apparatus mainly has the following issues:

(1) Steam produced by flash distillation is discharged to the environment, such that a large amount of heat carried by the waste water is directly discharged into air, causing huge waste of energy.

(2) Steam is directly discharged into air to form a phenomenon of "white dragon" in the production region, and acidic substances containing PT acids and the like in the steam cause serious pollution to the environment.

(3) The PTA mother liquid enters into the film processing system after cooling, and due to separation out of solid particles of the PT acid, it easily causes blockage of the film processing system.

SUMMARY

In order to solve the issues of the existing PTA mother liquid processing apparatus, an object of the present invention is to provide a method of recycling waste heat and PT acids of a PTA mother liquid. The method achieves high efficient multistage utilization of heat of the PTA mother liquid by using high efficient multistage flash distillation technology, low temperature cogeneration technology, heat pump heating and cooling technology, and low temperature crystallization technology. Through this method, recycling of heat in the PTA mother liquid can be achieved, and deficiencies of the existing industrial apparatus are solved.

The object of the present invention is realized in such way:

The present invention provides a method of recycling mother liquid of a pure terephthalic acid (PTA) refining unit, comprising steps of:

multistage flash distillation cooling step: the mother liquid of the PTA refining unit enters a high efficient multistage flash tower (1) including at least Nth stage flash zones, and performs (N−1)th stage flash distillation in the high efficient multistage flash tower (1);

the Nth stage flash zone in the high efficient multistage flash tower (1) is a flash distillation cooling zone, where no flash distillation is performed, and the flash distillation cooling zone is between an (N−2)th stage flash zone and an (N−1)th stage flash zone;

waste heat utilization step: flash distillation steam produced in a first stage flash zone to an Mth stage flash zone enters a waste heat utilization unit; and P-methylbenzoic acid (PT acid) crystallization and recycling step: the mother liquid produced for the (N−1)th stage flash zone entering into a low temperature crystallization unit to crystallize and recycle the PT acid in the mother liquid of the PTA refining unit;

wherein, N=4~8, M=1~4, N>M, and N and M are both integers.

As regards to the method of recycling mother liquid of a PTA refining unit according to the present invention, the waste heat utilization unit preferably comprises a first waste heat utilization unit and a second waste heat utilization unit;

the first waste heat utilization unit is preferably a heating unit and/or a cooling unit, where a first flash distillation steam produced in the first flash zone enters;

the second waste heat utilization unit is preferably a power generation unit, where flash distillation steam produced in the second stage flash zone to the Mth flash zone enters.

As regards to the method of recycling mother liquid of a PTA refining unit according to the present invention, the following steps are preferably and particularly performed in the heating unit:

one part of the first stage flash distillation steam from the high efficient multistage flash tower (1) enters a generator (21), where lithium bromide dilute solution is heated and evaporated; a steam condensate after heat exchange enters a third stage condensate buffer tank (39); the steam produced by evaporation enters a condenser (22) and is condensed under the action of circulating cooling water; working medium condensate produced by the condenser enters a heating evaporator (23), in which the working medium condensate is heated and evaporated by another part of the first stage flash distillation steam, and a cooling evaporator (25) respectively through a working medium circulating pump; a first stage flash distillation steam condensate after condensation enters the third stage condensate buffer tank (39); the heated and evaporated working medium steam enters a heating absorber (24), where lithium bromide concentrated solution is in an unsaturated state, thereby absorbing the working medium steam, during the course of which a large amount of heat is released; a condensate from a fourth stage condensate delivery pump (35) enters the heating absorber (24) to be heated; and the heated condensate enters a second stage condensate buffer tank (34) and performs flash distillation therein to produce medium, low pressure steam, which enters subsequent system for use.

As regards to the method of recycling mother liquid of a PTA refining unit according to the present invention, the following steps are preferably and particularly performed in the cooling unit:

working medium condensate entering the cooling evaporator (25) is evaporated under the action of heating of low-temperature water; working medium steam produced by evaporation enters a cooling absorber (26), where lithium bromide concentrated solution is in an unsaturated state, thereby absorbing the working medium steam; a large amount of heat released during the course of the absorption is cooled by circulating cooling water, and the low-temperature water after heat exchange in the cooling evaporator (25) is cooled down, thereby obtaining freeze water with lower temperature;

one part of the freeze water produced by the cooling evaporator (25) enters an air heat exchanger (36) to cool air at an inlet of an air compressor; the freeze water after heat exchange enters a freeze water buffer tank (37), and is delivered to the cooling evaporator (25) through a freeze water delivery pump (38) for recycling; and another part of the freeze water enters the high efficient multistage flash tower (1) to cool the flash distillation steam.

As regards to the method of recycling mother liquid of a PTA refining unit according to the present invention, the following steps are preferably and particularly performed in the power generation unit:

the second stage flash zone to the Mth flash zone connect with heat exchangers, respectively, while the respective heat exchangers are connected in series, such that the steam produced by the high efficient multistage flash tower (1) can gasify solvent in the heat exchangers;

flash distillation steam from the Mth flash zone performs indirect heat exchange with solvent from a solvent delivery pump (8) in a first stage heat exchanger connected thereto, and a steam condensate after heat exchange is discharged into a first stage condensate buffer tank (9);

the solvent after being heated in the previous step enters the next stage heat exchanger connected to the first stage heat exchanger in series, and a steam condensate after heat exchange is discharged into the first stage condensate buffer tank (9);

repeating heat exchange steps of the above solvent and the heat distillation steam in the flash zones;

solvent steam after gasification enters a steam turbine (5) to push the steam turbine so as to do work and generate power; then the solvent steam after doing work enters a solvent condenser (6); and a solvent condensate produced by condensation enters a solvent buffer tank (7) and is delivered to the first stage heat exchanger under the action of a solvent delivery pump (8), thereby completing circulation process of converting a part of waste heat in the PTA mother liquid into electric energy; and the condensate in the first stage condensate buffer tank (9) is delivered to subsequent system for use under the action of a first stage condensate delivery pump (10).

As regards to the method of recycling mother liquid of a PTA refining unit according to the present invention, the following steps are preferably and particularly performed in the low temperature crystallization unit:

the (N−2)th flash zone in the high efficient multistage flash tower (1) connects to a Venturi ejector (12); the Nth flash zone in the high efficient multistage flash tower (1) is a flash distillation cooling zone and connects to a second stage condensate delivery pump (13);

the mother liquid produced in the (N−1)th flash zone enters a crystallization tank (15), in which a large amount of crystallized PT acids is separated out, the remaining liquid containing small amount of solid impurities after crystallization sequentially enters a plurality of series connected filters under the action of pressure of a first stage mother liquid delivery pump (16) while solid particles are left and discharged through bottoms of the filters; the filtered mother liquid enters a mother liquid buffer tank (19), and enters the Venturi ejector (12) under the action of a second stage mother liquid delivery pump (20) to condense flash distillation steam from the (N−2)th flash zone; and the condensate after condensation is delivered to subsequent film processing system under the action of the second stage condensate delivery pump (13).

As regards to the method of recycling mother liquid of a PTA refining unit according to the present invention, N is 8, and M is 4.

As regards to the method of recycling mother liquid of a PTA refining unit according to the present invention, the mother liquid of the PTA refining unit has a temperature of preferably 140° C. to 150° C.

As regards to the method of recycling mother liquid of a PTA refining unit according to the present invention, a solvent of the solvent delivery pump (8) is preferably a 1,1,1,3,3-pentafluoropropane.

As regards to the method of recycling mother liquid of a PTA refining unit according to the present invention, the lithium bromide dilute solution has a mass concentration of preferably 56% to 60%, and the lithium bromide concentrated solution has a mass concentration of preferably 60% to 64%.

As regards to the method of recycling mother liquid of a PTA refining unit according to the present invention, the plurality of series connected filters are preferably series connection of first stage filters (17) and second stage filters (18), and filter cloths are provided in the plurality of series connected filters.

As regards to the method of recycling mother liquid of a PTA refining unit according to the present invention, N is 8, and M is 4. The specific steps can be described as follows:

a. firstly, mother liquid of a PTA refining unit enters into a high efficient multistage flash tower (1), where multistage flash distillation occurs, first stage flash distillation is performed in a first flash zone (I), and produced flash distillation steam enters into a generator (21) and a heating evaporator (23);

a condensate after the first stage flash distillation enters into a second flash zone (II) to perform second stage flash distillation, and flash distillation steam produced by flash distillation enters into a third stage heat exchanger (2);

a condensate after the second stage flash distillation enters into a third flash zone (III) to perform third stage flash distillation, and flash distillation steam produced by flash distillation enters into a second stage heat exchanger (3);

a condensate after the third stage flash distillation enters into a fourth flash zone (IV) to perform fourth stage flash distillation, and flash distillation steam produced by flash distillation enters into a first stage heat exchanger (4);

a condensate after the fourth stage flash distillation enters into a fifth flash zone (V) to perform fifth stage flash distillation, flash distillation steam produced by flash distillation enters into a steam condenser (11) to be condensed under the action of circulating cooling water, and a steam condensate after condensation enters into subsequent system for use;

a condensate after the fifth stage flash distillation enters into a sixth flash zone (VI), and flash distillation steam produced by flash distillation enters into a Venturi ejector (12);

a condensate after the sixth stage flash distillation enters into a seventh flash zone (VII), flash distillation steam produced by flash distillation is condensed under the action of freeze water, and a flash distillation condensate after condensation enters into a freeze water buffer tank (37) for use as supplementing water for preparing the freeze water under the action of a third condensate delivery pump (14);

b. the flash distillation steam from the fourth flash zone (IV) performs indirect heat exchange with a solvent from a solvent delivery pump (8) in the first stage heat exchange (4), and a steam condensate after heat exchange is discharged into a first condensate buffer pump (9);

a solvent after being heated by the first stage heat exchange (4) enters into the second heat exchange (3), and a steam condensate after heat exchange is discharged into the first condensate buffer pump (9);

a solvent after being heated by the second stage heat exchange (3) enters into the third heat exchange (2) to be gasified, and a steam condensate after heat exchange is discharged into the first condensate buffer pump (9);

the gasified solvent steam enters into a steam turbine (5) to push the steam turbine to do work and generate power, the solvent steam after doing work enters into a solvent condenser (6), a solvent condensate produced by condensation enters into a solvent buffer tank (7), and then is delivered to the first stage heat exchanger (4) under the action of the solvent delivery pump (8), thereby completing circulation process of converting a part of waste heat in the PTA mother liquid into electric energy;

a condensate in the first condensate buffer pump (9) is delivered to subsequent system for use under the action of a first stage condensate delivery pump (10);

c. the PTA mother liquid after flash distillation in the seven flash zone (VII) enters into a crystallization tank (15), a large amount of crystallized PT acids are separated out in the crystallization tank (15), the remaining liquid containing small amount of solid impurities after crystallization sequentially enters into a plurality of series connected filters under the action of pressure of a first stage mother liquid delivery pump (16) while solid particles are left and discharged from bottom of the filters, the filtered mother liquid enters into a mother liquid buffer tank (19), and enters into the Venturi ejector (12) under the action of a second stage mother liquid delivery pump (20) to condense the flash distillation steam from the sixth flash zone (VI), and a condensate after condensation is delivered to subsequent film processing system under the action of the second stage condensate delivery pump (13);

d. the first stage flash distillation steam from the high efficient multistage flash tower (1) having one part enters into a generator (21), where lithium bromide dilute solution is heated and evaporated, a steam condensate after heat exchange enters into a third stage condensate buffer tank (39), the steam produced by evaporation enters into a condenser (22) and condensed under the action of circulating cooling water, a working medium condensate produced by the condenser enters into a heating evaporator (23), in which the working medium condensate is heated and evaporated by another part of the first stage flash distillation steam, and a cooling evaporator (25) respectively through a working medium circulating pump, a first stage flash distillation steam condensate after condensation enters into the three stage condensate buffer tank (39), the heated and evaporated working medium condensate enters into a heating absorber (24), where lithium bromide concentrated solution is in an unsaturated state, thereby absorbing the working medium steam, during which a large amount of heat is released, a condensate from a fourth stage condensate delivery pump (35) enters into the heating absorber (24) to be heated, and the heated condensate enters into a second stage condensate buffer tank (34), where flash distillation occurs to produce medium and low pressure steam, which enters into subsequent system for use;

e. the working medium condensate enters into the cooling evaporator (25) to be evaporated under the action of heating of low-temperature water, working medium steam produced by evaporation enters into a cooling absorber (26), where lithium bromide concentrated solution is in an unsaturated state, thereby absorbing the working medium steam, during which a large amount of heat is released, and is cooled by circulating cooling water, and the low-temperature water after heat exchange in the cooling evaporator (25) is cooled down, thereby obtaining freeze water with lower temperature;

f. the freeze water produced by the cooling evaporator (25) having one part enters into an air heat exchanger (36) to cool air at an inlet of an air compressor, the freeze water after heat exchange enters into a freeze water buffer tank (37), and is delivered to the cooling evaporator (25) through a freeze water delivery pump (38) for recycling, and another part enters into the high efficient multistage flash tower (1) to cool the seventh flash distillation steam.

The present invention may be further described as follows:

A method of recycling mother liquid waste heat and PT acids of a PTA refining unit, particularly comprising steps of:

a. firstly, PTA mother liquid under a certain temperature from upstream enters into a high efficient multistage flash tower 1, where the PTA mother liquid performs first stage flash distillation in a first flash zone I, and flash distillation steam produced by flash distillation enters into a generator 21 and a heating evaporator 23; a condensate after the first stage flash distillation enters into a second flash zone II of the high efficient multistage flash tower 1, where the PTA mother liquid performs second stage flash distillation, and flash distillation steam produced by flash distillation enters into a third stage heat exchanger 2; a condensate after the second stage flash distillation enters into a third flash zone III, where the PTA mother liquid performs third stage flash distillation, and flash distillation steam produced by flash distillation enters into a second stage heat exchanger 3; a condensate after the third stage flash distillation enters into a fourth flash zone IV, where the PTA mother liquid performs fourth stage flash distillation, and flash distillation steam produced by flash distillation enters into a first stage heat exchanger 4; a condensate after the fourth stage flash distillation enters into a fifth flash zone V, where the PTA mother liquid performs fifth stage flash distillation, flash distillation steam produced by flash distillation enters into a steam condenser 11 to be condensed under the action of circulating cooling water, and a steam condensate after condensation enters into subsequent system for use; a condensate after the fifth stage flash distillation enters into a sixth flash zone VI, where the PTA mother liquid performs sixth stage flash distillation, and flash distillation steam produced by flash distillation enters into a Venturi ejector 12; a condensate after the sixth stage flash distillation enters into a seventh flash zone VII, where the PTA mother liquid performs seventh stage flash distillation, flash distillation steam produced by flash distillation is condensed under the action of freeze water, and a flash distillation condensate after condensation enters into a freeze water buffer tank 37 for use as supplementing water for preparing the freeze water under the action of a third condensate delivery pump 14;

b. the flash distillation steam from the fourth flash zone IV performs indirect heat exchange with a solvent (using a R245fa solvent) from a solvent delivery pump 8 in the first stage heat exchange 4, where the solvent is heated to a certain temperature, and a steam condensate after heat exchange is discharged into a first condensate buffer pump 9; a solvent after being heated by the first stage heat exchange 4 enters into the second heat exchange 3, where the solvent performs indirect heat exchange with the flash distillation steam from the third flash zone III, and the solvent is further heated, and a steam condensate after heat exchange is discharged into the first condensate buffer pump 9; a solvent after being heated by the second stage heat exchange 3 enters into the third heat exchange 2, where the solvent performs indirect heat exchange with the flash distillation steam from the second flash zone II, and the solvent is gasified, and a steam condensate after heat exchange is discharged into the first condensate buffer pump 9; the gasified solvent steam enters into a steam turbine 5 to push the steam turbine to do work and generate electricity, the solvent steam after doing work enters into a solvent condenser 6 to be condensed under the action of circulating cooling water, a solvent condensate produced by condensation enters into a solvent buffer tank 7, and then is delivered to the first stage heat exchanger 4 under the action of the solvent delivery pump 8, thereby completing circulation process of converting a part of waste heat in the PTA mother liquid into electric energy; a condensate in the first condensate buffer pump 9 is delivered to subsequent system for use under the action of a first stage condensate delivery pump 10;

c. the PTA mother liquid after flash distillation in the seven flash zone VII enters into a crystallization tank 15, since the PTA mother liquid is low in temperature, a large amount of crystallized PT acids are separated out in the crystallization tank 15, the remaining liquid containing small amount of solid impurities after crystallization sequentially enters into first stage filters 17 and second stage filters 18, where filter cloths are arranged, under the action of pressure of a first stage mother liquid delivery pump 16 while solid particles are left and discharged from bottom of the filters, the filtered mother liquid enters into a mother liquid buffer tank 19, and enters into the Venturi ejector 12 under the action of a second stage mother liquid delivery pump 20, where the flash distillation steam from the sixth flash zone VI is condensed, and a condensate after condensation is delivered to subsequent film processing system under the action of the second stage condensate delivery pump 13;

d. the first stage flash distillation steam from the high efficient multistage flash tower 1 having one part enters into a generator 21, where lithium bromide dilute solution with a certain concentration is heated and evaporated, a steam condensate after heat exchange enters into a third stage condensate buffer tank 39, the steam produced by evaporation enters into a condenser 22 and condensed under the action of circulating cooling water, a working medium condensate produced by the condenser enters into a heating evaporator 23, in which the working medium condensate is heated and evaporated by another part of the first stage flash distillation steam, and a cooling evaporator 25 respectively through a working medium circulating pump, a first stage flash distillation steam condensate after condensation enters into the third stage condensate buffer tank 39, the heated and evaporated working medium condensate enters into a heating absorber 24, where lithium bromide concentrated solution is in an unsaturated state, thereby absorbing the working medium steam, during which a large amount of heat is released, a condensate from a fourth stage condensate delivery pump 35 enters into the heating absorber 24 to be heated, and the heated condensate enters into a second stage condensate buffer tank 34, where flash distillation occurs to produce medium and low pressure steam under a certain temperature, which enters into subsequent system for use;

e. the working medium condensate enters into the cooling evaporator 25 to be evaporated under the action of heating of low-temperature water, working medium steam produced by evaporation enters into a cooling absorber 26, where lithium bromide concentrated solution is in an unsaturated state, thereby absorbing the working medium steam, during which a large amount of heat is released, and is cooled by circulating cooling water, and the low-temperature water after heat exchange in the cooling evaporator 25 is cooled down, thereby obtaining freeze water with lower temperature;

f. the freeze water produced by the cooling evaporator 25 having one part enters into an air heat exchanger 36 to cool air at an inlet of an air compressor, the freeze water after heat exchange enters into a freeze water buffer tank 37, and is delivered to the cooling evaporator 25 through a freeze water delivery pump 38 for recycling, and another part enters into the high efficient multistage flash tower 1 to cool the seventh flash distillation steam. A vacuum degree of the present system is maintained by a first stage vacuum pump 41, a second stage vacuum pump 42 and a third stage vacuum pump 43.

Advantageous effects of the present invention are as follows:

1. The present invention comprehensively utilizes the original steam discharged to the environment by stages, and a part of waste heat in the PTA mother liquid is used for generating electricity, and preparing high quality steam and freeze water, thereby achieving recycling of heat.

2. The present invention recycles PT acid crystallization in the PTA mother liquid, reduces influence of the PT acid crystallization on subsequent system, can supply crystallized process water to the subsequent film processing system, and solves the issue of blockage of the film processing system using low temperature crystallization technology.

3. The present invention recycles the original steam discharged to the environment, and solves the issue of environment pollution.

4. The mother liquid processing method provided by the present invention is low in equipment investment, also can directly generate electricity using byproducts, produce high quality steam for utilization, and use produced freeze water for cooling air that enters into the air compressor, which largely reduces electricity consumption of the air compressor, and reduces operation costs of the PTA apparatus. Therefore, the mother liquid processing method provided by the present invention can produce huge economic benefits.

DETAILED EMBODIMENTS OF THE DESCRIPTION

Examples of the present invention are explicitly explained below: the Examples are carried out with detailed embodiments and procedures on the premise of the technical solution of the present invention, but the extent of protection of the present invention is not limited thereto. The below Examples do not indicate the experimental method with specific conditions, and they often follow the conventional conditions.

Figure 1:
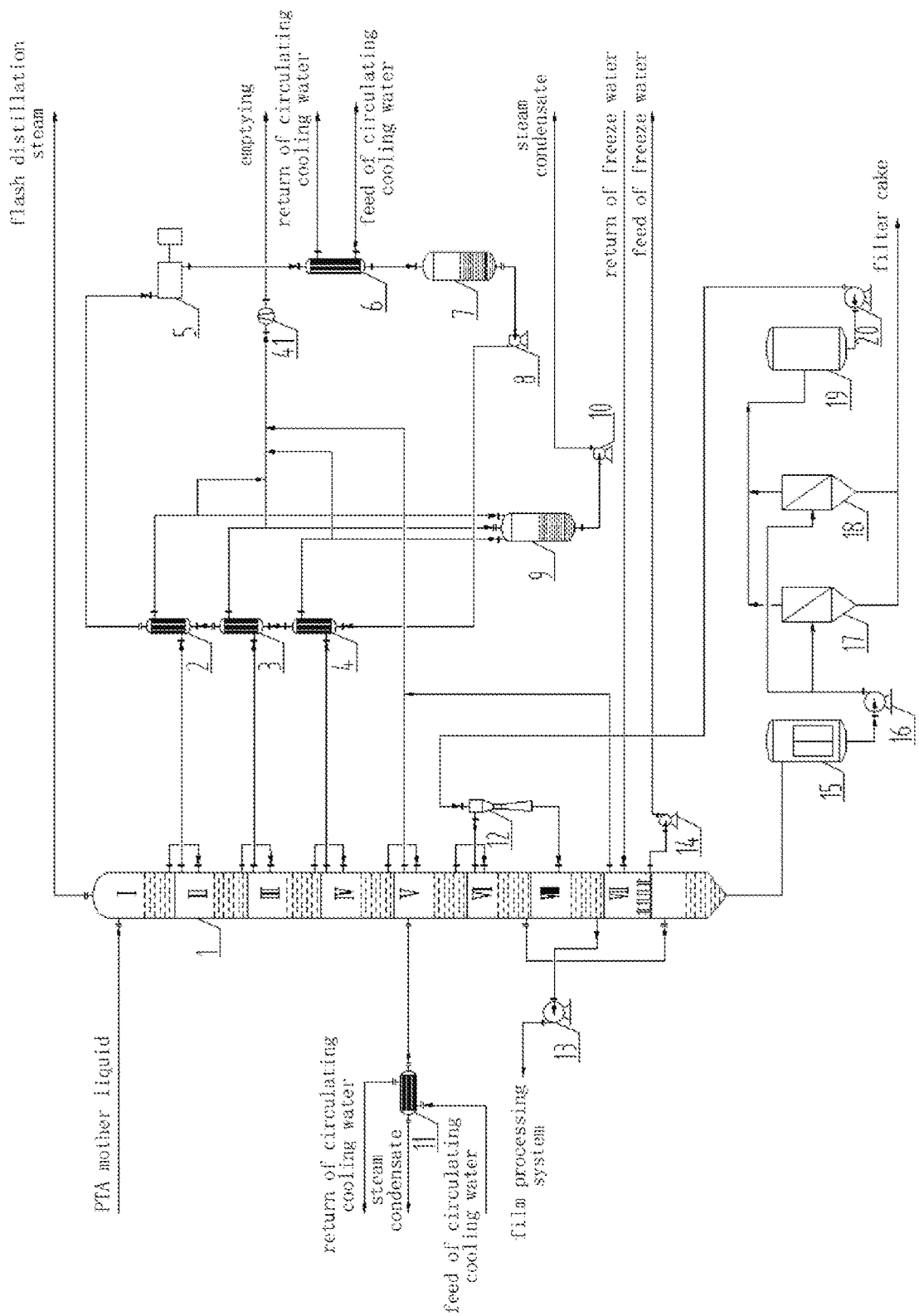
FIGS. 1 and 2 are flow diagrams of processes according to the present invention.
Figure 2:
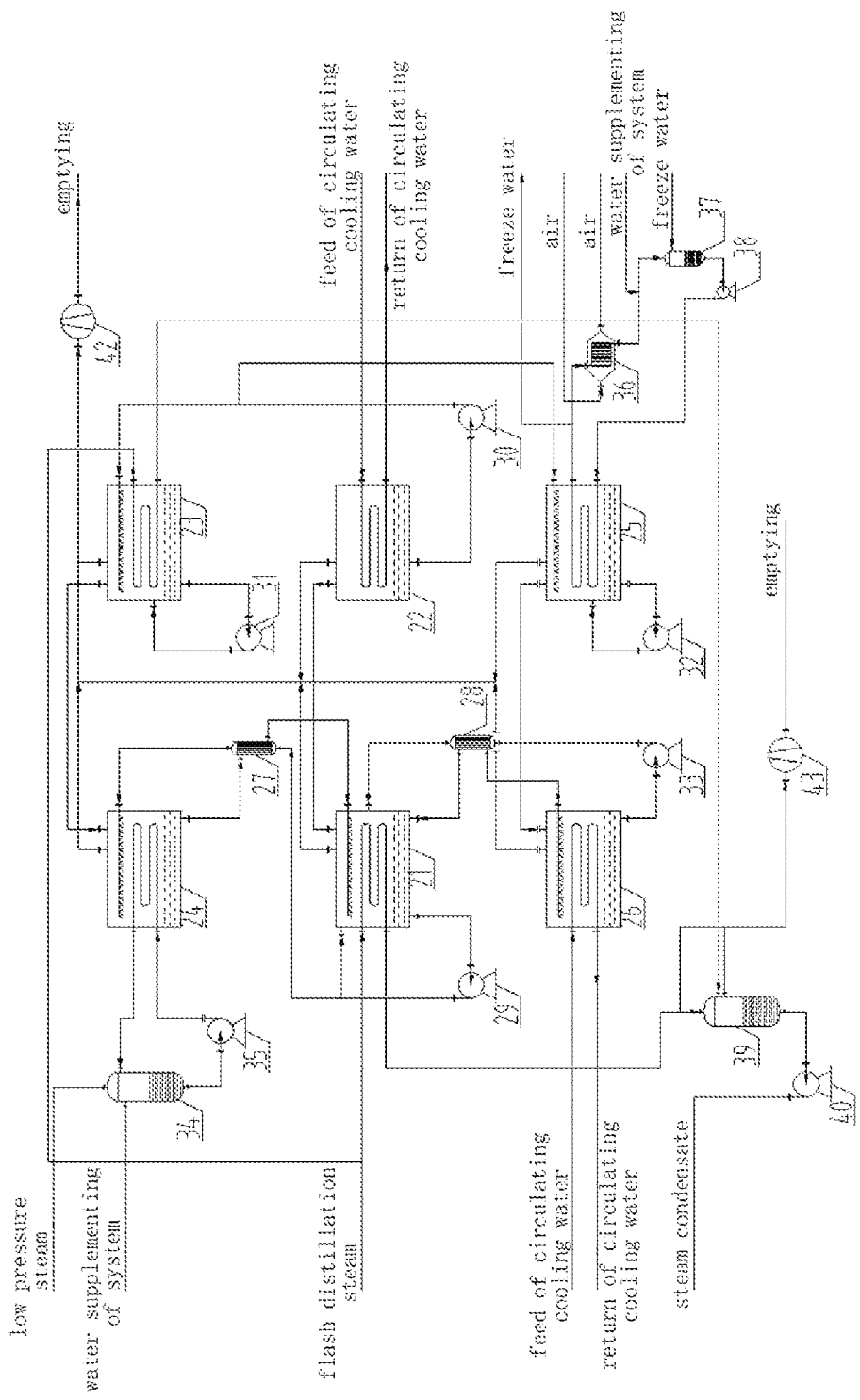

Referring to FIGS. 1 and 2, taking the example that N is 8, and M is 4, the specific embodiment of the present invention is further described as follows:

(1) firstly, mother liquid of a PTA refining unit having a temperature of 140° C. to 150° C. enters into a first stage flash zone I of a high efficient multistage flash tower 1, where PTA mother liquid performs vacuum flashing to produce a saturated steam at about 100° C., which enters into a subsequent generator 21 and a heating evaporator 23; the PTA mother liquid at 100° C. after flash distillation enters into a second stage flash zone II, where vacuum flashing is performed to produce a saturated steam at about 90° C., which enters into a third heat exchanger 2; the PTA mother liquid at 90° C. after flash distillation enters into a third stage flash zone III, where vacuum flashing is performed to produce a saturated steam at about 80° C., which enters into a second heat exchanger 3; the PTA mother liquid at 80° C. after flash distillation enters into a fourth stage flash zone IV, where vacuum flashing is performed to produce a saturated steam at about 70° C., which enters into a first heat exchanger 4; the PTA mother liquid at 70° C. after flash distillation enters into a fifth stage flash zone V, where vacuum flashing is performed to produce a saturated steam at about 60° C., which enters into a steam condenser 11, and is cooled using circulating cooling water, and a steam condensate after condensation enters into subsequent system; the PTA mother liquid at 60° C. after flash distillation enters into a sixth stage flash zone VI, where vacuum flashing is performed to produce a saturated steam at about 40° C., which enters into a Venturi ejector 12; the PTA mother liquid at 40° C. after flash distillation enters into a seventh stage flash zone VII, where vacuum flashing is performed to produce a saturated steam at about 25° C., where the produced saturated steam performs direct contact heat exchange with freeze water from a cooling evaporator 25, the saturated steam is condensed, and a condensate after condensation enters into a freeze water buffer tank 37 under the action of a third stage condensate delivery pump.

(2) In the low temperature cogeneration system, a circulating solvent is R245fa, the saturated steam at 70° C. from the fourth stage flash zone IV enters into the first stage heat exchanger 4 to perform indirect heat exchange with a solvent from a solvent delivery pump 8, the solvent is heated to 55° C. to 60° C., and a steam condensate after heat exchange enters into a first stage condensate buffer tank 9; the solvent after being heated by the first stage heat exchanger 4 enters into the second stage heat exchanger 3, where it performs indirect heat exchange with the saturated steam at about 80° C. from the third flash zone III, and the solvent is heated to 65° C. to 70° C., and a steam condensate after heat exchange enters into the first stage condensate buffer tank 9; the solvent after being heated by the second stage heat exchanger 3 enters into the third stage heat exchanger 2, where it performs indirect heat exchange with the saturated steam at about 90° C. from the second flash zone II, and the solvent is evaporated to produce a solvent steam at 75° C. to 85° C., and a steam condensate after heat exchange enters into the first stage condensate buffer tank 9. The solvent steam at 75° C. to 85° C. enters into a steam turbine 5 to push the steam turbine to do work and generate electricity, the solvent steam after doing work is about 45° C. to 50° C., enters into a solvent condenser 6, and is condensed using circulating cooling water, and a solvent condensate after condensation enters into a solvent buffer tank 7, and enters into the first stage heat exchanger 4 under the action of the solvent circulating pump 8, thereby completing circulation process of low temperature cogeneration. The steam condensate in the first stage condensate buffer tank 9 is delivered to subsequent system under the action of a first stage condensate delivery pump 10.

(3) The PTA mother liquid at 25° C. from the seventh flash zone VII enters into a crystallization tank 15, where a large amount of PT acids in the PTA mother liquid are crystallized, the PTA mother liquid after crystallization sequentially enters into first stage filters 17 and second stage filters 18 under the action of a first stage mother liquid delivery pump 16 to remove solid impurities contained in the PTA mother liquid, the filtered PTA mother liquid enters into a mother liquid buffer tank 19, and enters into the Venturi ejector 12 through a second stage mother liquid delivery pump 20, where the PTA mother liquid at 25° C. condenses the saturated steam at 40° C. in the sixth flash zone VI, and the produced condensate enters into a flash distillation cooling zone VIII, and enters into subsequent film processing system under the action of a second stage condensate delivery pump (VIII is between VI and VII, where no flash distillation occurs, and flash distillation occurs in other seven zones).

(4) The saturated steam at 100° C. from the first stage flash zone I having one part enters into the generator 21 for use as a heat source, and another part enters into the heating evaporator 23 for use as the heat source, lithium bromide solution is used as a circulating solvent, and water steam as a working medium in the heat pump heating and cooling technologies; in the generator 21, the lithium bromide solution with a concentration of 56% to 60% is heated by the saturated steam at 100° C. to be evaporated, and the produced working medium steam at 80° C. to 90° C. enters into a condenser 22, where the working medium steam performs indirect heat exchange with circulating cooling water to obtain a steam condensate, i.e., a working medium condensate, at about 40° C., one part of which enters into the heating evaporator 23 through a first stage working medium circulating pump, and one part enters into the cooling evaporator 25; in the heating evaporator 23, the working medium condensate is evaporated under the action of a heat source at 100° C. to produce a working medium steam at about 90° C., in order to ensure evaporation smoothly, the working medium condensate is circulated and evaporated compulsorily through a second stage working medium circulating pump 31, the working medium steam produced by the heating evaporator 23 enters into a heating absorber 24, where lithium bromide solution has a concentration of 60% to 64%, and the lithium bromide solution is in an unsaturated state, such that the working medium steam can be absorbed, during which the working medium steam releases a large amount of heat, condensate from a fourth stage condensate delivery pump 35 enters into the heating absorber 24, and absorbs the released heat, a temperature of the condensate rises to 135° C. to 140° C., and subsequently, the heated condensate enters into a second stage condensate buffer tank 34, where flash distillation occurs to produce a saturated steam at about 130° C., which enters into subsequent system for use; after the 56%~60% lithium bromide solution is evaporated in the generator 21, 60%~64% lithium bromide solution is produced, and enters into a first stage solvent heat exchanger 27 under the action of a first stage lithium bromide circulating pump 29, and after the 60%~64% lithium bromide solution absorbs the working medium steam in the heating absorber, the 56%~60% lithium bromide solution is produced, and enters into the first stage solvent heat exchanger 27, where it performs indirect heat exchange with the lithium bromide solution from the generator, thereby completing the heating process of the heat pump.

(5) The working medium condensate at 40° C. entering into the cooling evaporator 25 absorbs heat of low-temperature water at about 15° C. from a freeze water delivery pump 38, the working medium condensate is evaporated to produce a working medium steam at 5° C., in order to ensure evaporation of the working medium condensate smoothly, the working medium condensate is circulated and evaporated compulsorily through a third stage working medium circulating pump 32, the low-temperature water at 15° C. after absorbing heat produces freeze water at 5° C. to 10° C., and the produced working medium steam at 5° C. enters into a cooling absorber 26, where the lithium bromide solution with a concentration of 60%~64% absorbs the working medium steam, during which heat is released, and is cooled using circulating cooling water, and the 56%~60% lithium bromide solution after absorption performs indirect heat exchange with the 60%~64% lithium bromide solution from the evaporator 21 in a second stage solvent exchanger 28, thereby completing the cooling process of the heat pump.

(6) The freeze water at 5° C. to 10° C. from the cooling evaporator 25 having one part enters into an air exchanger 36, where air entering into an air compressor is cooled from 25° C. to about 15° C., the freeze water after heat exchange enters into the freeze water buffer tank 37, and is delivered to the cooling evaporator 25 through the freeze water delivery pump 38 for circulation, and another part enters into the seventh flash zone to condense a saturated steam at 25° C. produced by flash distillation. The saturated steam at 100° C. going to the generator 21 and the heating evaporator 23 enters into a third stage condensate buffer tank 39 through the condenser, and is delivered to subsequent system for use under the action of a fifth stage condensate delivery pump 40.

The invention claimed is:

1. A method of recycling mother liquid of a pure terephthalic acid (PTA) refining unit, comprising steps of:
   multistage flash distillation cooling step: the mother liquid of the PTA refining unit enters a multistage flash tower including at least Nth stage flash zones, and performs (N−1)th stage flash distillation in the multistage flash tower;
   the Nth stage flash zone in the multistage flash tower is a flash distillation cooling zone, where no flash distillation is performed, and the flash distillation cooling zone is between an (N−2)th stage flash zone and an (N−1)th stage flash zone;
   waste heat utilization step: flash distillation steam produced in a first stage flash zone to an Mth stage flash zone enters a waste heat utilization unit; and
   P-methylbenzoic acid (PT acid) crystallization and recycling step: the mother liquid produced in the (N−1)th stage flash zone enters a low temperature crystallization unit to crystallize and recycle the PT acid in the mother liquid of the PTA refining unit;
   wherein, N=4~8, M=1~4, N>M, and N and M are both integers.

2. The method of recycling mother liquid of a PTA refining unit according to claim 1, wherein the waste heat utilization unit comprises a first waste heat utilization unit and a second waste heat utilization unit;
   the first waste heat utilization unit is a heating unit and/or a cooling unit, where a first flash distillation steam produced in the first flash zone enters;
   the second waste heat utilization unit is a power generation unit, where flash distillation steam produced in the second stage flash zone to the Mth flash zone enters.

3. The method of recycling mother liquid of a PTA refining unit according to claim 2, wherein:
   the following steps are performed in the heating unit:
   one part of the first stage flash distillation steam from the multistage flash tower enters a generator, where lithium bromide dilute solution is heated and evaporated; a steam condensate after heat exchange enters a third stage condensate buffer tank; the steam produced by evaporation enters a condenser and is condensed under the action of circulating cooling water; working medium condensate produced by the condenser enters a heating evaporator, in which the working medium condensate is heated and evaporated by another part of the first stage flash distillation steam, and a cooling evaporator respectively through a working medium circulating pump; a first stage flash distillation steam condensate after condensation enters the third stage condensate buffer tank; the heated and evaporated working medium steam enters a heating absorber, where lithium bromide concentrated solution is in an unsaturated state, thereby absorbing the working medium steam, during the course of which a large amount of heat is released; a condensate from a fourth stage condensate delivery pump enters the heating absorber to be heated; and the heated condensate enters a second stage condensate buffer tank and performs flash distillation therein to produce medium, low pressure steam, which enters subsequent system for use.

4. The method of recycling mother liquid of a PTA refining unit according to claim 2, wherein:
   the following steps are performed in the cooling unit:
   working medium condensate entering the cooling evaporator is evaporated under the action of heating of low-temperature water; working medium steam produced by evaporation enters a cooling absorber, where lithium bromide concentrated solution is in an unsaturated state, thereby absorbing the working medium steam; a large amount of heat released during the course of the absorption is cooled by circulating cooling water, and the low-temperature water after heat exchange in the cooling evaporator is cooled down, thereby obtaining freeze water with lower temperature;
   one part of the freeze water produced by the cooling evaporator enters an air heat exchanger to cool air at an inlet of an air compressor; the freeze water after heat exchange enters a freeze water buffer tank, and is delivered to the cooling evaporator through a freeze water delivery pump for recycling; and another part of the freeze water enters the multistage flash tower to cool the flash distillation steam.

5. The method of recycling mother liquid of a PTA refining unit according to claim 2, wherein:
   the following steps are performed in the power generation unit:
   the second stage flash zone to the Mth flash zone connect with heat exchangers, respectively, while the respective heat exchangers are connected in series, such that the steam produced by the multistage flash tower can gasify solvent in the heat exchangers;
   flash distillation steam from the Mth flash zone performs indirect heat exchange with solvent from a solvent delivery pump in a first stage heat exchanger connected thereto, and a steam condensate after heat exchange is discharged into a first stage condensate buffer tank;
   the solvent after being heated in the previous step enters the next stage heat exchanger connected to the first stage heat exchanger in series, and a steam condensate after heat exchange is discharged into the first stage condensate buffer tank;

repeating heat exchange steps of the above solvent and the heat distillation steam in the flash zones;

solvent steam after gasification enters a steam turbine to push the steam turbine so as to do work and generate power; then the solvent steam after doing work enters a solvent condenser; and a solvent condensate produced by condensation enters a solvent buffer tank and is delivered to the first stage heat exchanger under the action of a solvent delivery pump, thereby completing circulation process of converting a part of waste heat in the PTA mother liquid into electric energy; and the condensate in the first stage condensate buffer tank is delivered to subsequent system for use under the action of a first stage condensate delivery pump.

6. The method of recycling mother liquid of a PTA refining unit according to claim 1, wherein:

the following steps are performed in the low temperature crystallization unit:

the (N−2)th flash zone in the multistage flash tower connects to a Venturi ejector; the Nth flash zone in the multistage flash tower is a flash distillation cooling zone and connects to a second stage condensate delivery pump;

the mother liquid produced in the (N−1)th flash zone enters a crystallization tank, in which a large amount of crystallized PT acids is separated out; the remaining liquid containing small amount of solid impurities after crystallization sequentially enters a plurality of series connected filters under the action of pressure of a first stage mother liquid delivery pump while solid particles are left and discharged through bottoms of the filters;

the filtered mother liquid enters a mother liquid buffer tank, and enters the Venturi ejector under the action of a second stage mother liquid delivery pump to condense flash distillation steam from the (N−2)th flash zone; and the condensate after condensation is delivered to subsequent film processing system under the action of the second stage condensate delivery pump.

7. The method of recycling mother liquid of a PTA refining unit according to claim 1, wherein N is 8, and M is 4.

8. The method of recycling mother liquid of a PTA refining unit according to claim 6, wherein N is 8, and M is 4.

9. The method of recycling mother liquid of a PTA refining unit according to claim 7, wherein the mother liquid of the PTA refining unit has a temperature of 140° C. to 150° C.

10. The method of recycling mother liquid of a PTA refining unit according to claim 5, wherein a solvent of the solvent delivery pump is 1,1,1,3,3-pentafluoropropane.

11. The method of recycling mother liquid of a PTA refining unit according to claim 3, wherein the lithium bromide dilute solution has a mass concentration of 56% to 60%, and the lithium bromide concentrated solution has a mass concentration of 60% to 64%.

12. The method of recycling mother liquid of a PTA refining unit according to claim 6, wherein the plurality of series connected filters are series connection of first stage filters and second stage filters, and filter cloths are provided in the plurality of series connected filters.

* * * * *